United States Patent [19]

Ray et al.

[11] Patent Number: 5,663,069

[45] Date of Patent: Sep. 2, 1997

[54] MODIFIED LAMBDA BACTERIOPHAGE

[75] Inventors: Bryan L. Ray, Burlington; Edmund C. C. Lin, Boston; Roberto Crea, Belmont, all of Mass.

[73] Assignee: Medical Science Partners, Wellesley, Mass.

[21] Appl. No.: 590,708

[22] Filed: Dec. 8, 1995

Related U.S. Application Data

[63] Continuation of Ser. No. 53,866, Apr. 27, 1993, abandoned.

[51] Int. Cl.$^6$ .................... C12N 7/02; C12N 7/01; C07H 21/04; C07K 14/005
[52] U.S. Cl. .................. 435/235.1; 435/239; 536/23.72; 530/402
[58] Field of Search ..................... 435/235.1, 239; 536/23.72; 530/402

[56] References Cited

U.S. PATENT DOCUMENTS

| | | | |
|---|---|---|---|
| 3,717,705 | 2/1973 | Halmovich et al. | 424/12 |
| 4,703,008 | 10/1987 | Lin | 435/240.2 |
| 5,112,615 | 5/1992 | Ito et al. | 424/426 |
| 5,223,409 | 6/1993 | Ladner et al. | 435/69.7 |
| 5,403,484 | 4/1995 | Ladner et al. | 435/235.1 |

FOREIGN PATENT DOCUMENTS

| | | |
|---|---|---|
| WO88/06630 | 9/1988 | WIPO. |
| WO91/19818 | 12/1991 | WIPO. |

OTHER PUBLICATIONS van der Ende et al. (1982) *Nucleic Acids Research* 10:6849–6863.
Hurwitz et al. (1975) *Cancer Research* 35:1175–1181.
Muller et al. (1989) *Gene* 75:329–334.
Katsura in *Lambda II* (R.W. Hendrix, ed.) Cold Spring Harbor Labotatory Press, Cold Spring Harbor, N.Y. (1983), p. 331;.
Becker et al., *Immunochem.* 7:741–743 (1970).
Hurwitz et al., *Eur. J. Biochem.* 17:273–277 (1970).
Gurari et al., *Eur. J. Biochem.* 26:247–250 (1972).
Oger et al., *Proc. Natl. Acad. Sci.* (USA) 71:1554–1558 (1974).
Katsura, *Molec. Gen. Genet.* 148:31–42 (1976).
Katsura et al., *Virol.* 76:129–145 (1977).
Hohn, *Meth. Enzymol.* 68:299–309 (1979).
Shaw et al., *Genetics* 92:741–747 (1979).
*Advanced Bacterial Genetics* (Davis et al., eds.), Cold Spring Harbor Laboratory, Cold Spring Harbor, NY (1980) pp. 71 and 74–77.
Katsura, *J. Mol. Bio.* 146:493–512 (1981).
Lazzaroni et al., *J. Bacteriol.* 145:1351–1358 (1981).
Maniatis et al., *Molecular Cloning: A Laboratory Manual* Cold Spring Harbor Lab., CSH, NY pp. 150–170 and 395 (1982).
Sanger et al., *J. Mol. Biol.* 162:729–773 (1982).
Arber et al., *Lambda II* (Hendrix, ed.) Cold Spring Harbor Laboratory, Cold Spring Harbor, NY (1983) p. 438.
*Difco Manual*, (10th ed.), Difco Laboratories, Detroit, MI (1984) p. 572.
Wilchek et al., *Meth. Enzymol.* 104:3–55 (1984).
March et al., *Nature* 315:641–647 (1985).
Yanisch-Perron et al., *Gene* 33: 103–119 (1985).
Kasuda et al., *J. Biol. Chem.* 261:16161–16168 (1986).
Tao et al., *Biochem.* 25:7633–7639 (1986).
Black et al., *J. Biol. Chem.* 263:9437–9442 (1988).
*Laboratory Techniques in Biochemistry and Molecular Biology*, vol. 19, Elsevier Science Pub. Co., Amsteradam (1988)pp. 95–130.
Lin et al., *Science* 246:1023–1025 (1989).
Pluckthun et al., *Meth. Enzymol.* 178:497–515 (1989).
Sambrook et al., *Molecular Cloning: A Laboratory Manual*, Cold Spring Harbor Lab., Cold Spring Harbor, NY (1989) p. 17.13.
Ward et al., *Nature* 341:544–546 (1989).
Chalmers et al., *Appl. Environ. Microbiol.* 56:104–111 (1990).
Chaudhary et al., *Proc. Natl. Acad. Sci.* (USA) 87:1066–1070 (1990).
Devlin et al., *Science* 249:404–406 (1990).
Georgoussi et al., *Biochem. Biophys. Acta* 1055:69–74 (1990).
Scharf, "Cloning with PCR" in *PCR Protocols: A Guide to Methods & Applications* (Innis et al., eds.) Academic Press, San Diego, CA (1990) pp. 84–91.
Scott et al., *Science* 249:386–390 (1990).
Barbas et al., *Proc. Natl. Acad. Sci.* (USA) 88:7978–7982 (1991).
Foster, *Meth. Enzymol.* 204:114–125 (1991).
Garrard et al., *Bio/Technol.* 9:1373–1377 (1991).
Rampf et al., *FEBS Lett.* 280:27–31 (1991).
Chak et al., *Meth. Enzymol.* 207:546–555 (1992).
Kamata et al., *J. Biochem.* 111:546–552 (1992).
Katsura, J Mol Biol 146(4), pp. 493–512, 1981.

*Primary Examiner*—Marianne P. Allen
*Attorney, Agent, or Firm*—Hale and Dorr LLP

[57] ABSTRACT

Disclosed is a protein construct including a chemically modified lambdoid tail protein having a chemically reactive amino acid residue linked to a target molecule. Also disclosed is an infective lambdoid bacteriophage displaying on its outer surface the chemically modified tail protein. In addition, methods of detecting a molecule-of-interest in a solution and methods of detecting cells producing a molecule-of-interest which utilize the infective lambdoid bacteriophage having the chemically modified tail protein are disclosed.

5 Claims, 5 Drawing Sheets

```
             M  F  V  F  N  F  T  M  P  V  K
             ATGCCTGTACCAAATCCTACAATGCCGGTGAA

G  A  G  T  T  L  W  V  Y  K  G  S  G  D  P  Y
  AGGTGCCGGCACCACCCTGTGGGTTTATAAGGGGAGCGGTGACCCTTACG

A  N  P  L  S  D  V  D  W  S  R  L  A  K  V  K  D
  CGAATCCGCTTTCAGACGTTGACTCGTCGCGTCTGGCAAAAGTTAAAGAC

L  T  P  G  E  L  T  A  E  S  Y  D  D  S  Y  L  D
     CTGACGCCCGGCGAACTGACCGCTGAGTCCTATGACGACAGCTATCTCGA

D  E  D  A  D  W  T  A  T  G  Q  G  Q  K  S  A
   TGATGAAGATGCAGACTGGACTGCGACCGGGCAGGGGCAGAAATCTGCCG

G  D  T  S  F  T  L  A  W  M  P  G  E  Q  G  Q  Q
   GAGATACCAGCTTCACGCTGGCGTGGATGCCCGGAGAGCAGGGGCAGCAG

A  L  L  A  W  F  N  E  G  D  T  R  A  Y  K  I  R
   GCGCTGCTGGCGTGGTTTAATGAAGGCGATACCCGTGCCTATAAAATCCG

F  P  N  G  T  V  D  V  F  R  G  W  V  S  S  I
    CTTCCCGAACGGCACGGCACATGTGTTCCGTGGCTGGGTCAGCAGTATCG

G  K  A  V  T  A  K  E  V  I  T  R  T  V  K  V  T
   GTAAGGCGGTGACGGCGAAGGAAGTGATCACCCGCACGGTGAAAGTCACC

N  V  G  R  P  S  M  A  E  D  R  S  T  V  T  A  A
    AATGTGGGACGTCCGTCGATGGCAGAAGATCGCAGCACGGTAACAGCGGC

T  G  M  T  V  T  P  A  S  T  S  V  V  K  G  Q
    AACCGGCATGACCGTGACGCCTGCCAGCACCTCGGTGGTGAAAGGGCAGA

S  T  T  L  T  V  A  F  Q  P  E  G  V  T  D  K  S
   GCACCACGCTGACCGTGGCCTTCCAGCCGGAGGGCGTAACCGACAAGAGC

F  R  A  V  S  A  D  K  T  K  A  T  V  S  V  S  G
   TTTCGTGCGGTGTCTGCGGATAAAACAAAAGCCACCGTGTCGGTCAGTGG

M  T  I  T  V  N  G  V  A  A  G  K  V  N  I  P
     TATGACCATCACCGTGAACGGCGTTGCTGCAGGCAAGGTCAACATTCCGG

V  V  S  G  N  G  E  F  A  A  V  A  E  I  T  V  T
   TTGTATCCGGTAATGGTGAGTTTGCTGCGGTTGCAGAAATTACCGTCACC

A  C
   GCCTGT
```

MODIFIED LAMBDA BACTERIOPHAGE

This application is a file wrapper continuation of U.S. patent application Ser. No. 08/053,866, filed Apr. 27, 1993, now abandoned. This application is also related to U.S. patent application Ser. No. 08/299,249, entitled "Method of Detecting Compounds Utilizing Chemically Modified Lambdoid Bacteriophage", which is a file wrapper continuation of U.S. patent application Ser. No. 08/053,865, now abandoned.

FIELD OF THE INVENTION

This invention relates to the detection of compounds, and more specifically to methods for detecting and assaying for a molecule-of-interest and for cells producing molecules-of-interest utilizing a genetically and chemically modified lambdoid bacteriophage.

BACKGROUND OF THE INVENTION

Bacteriophages have been used in strategies for detecting molecules-of-interest. For example, a method employing the bacteriophage M13 has been used to assay for various proteins of interest. In this method M13 phage displaying peptides fused to pIII, a minor M13 coat protein, have been used to screen for protein binding molecules and antibodies (Scott et al. (1990) *Science* 249:386; Devlin et al. (1990) *Science* 249:404). Special M13-derived systems have been used to express antibodies as fusion proteins on the surface of the phage, and techniques have been developed to enrich the population for phage expressing antibodies with desired affinities for an antigen (Garrard et al. (1991) *Bio/Technol* 9:1373; Barbas et al. (1991) *Proc. Natl. Acad. Sci* (USA) 88:7978). However, the use of M13 in assay methods is limited because M13 infection is not immediately ascertainable. This is because infection by M13 does not provide the cell with compounds required for cell growth and does not lyse the cells.

The bacteriophage T4 has also been used in assays for various proteins. For example, T4 has been used to detect nerve growth factor (NGF) (Oger. et al. (1974) *Proc. Natl. Acad. Sci.* (USA) 71:1554–1558). In this assay, T4 was chemically coupled to NGF using glutaraldehyde. Glutaraldehyde reacts with lysine and cysteine residues as well as with α-NH$_3$ groups (see *Laboratory Techniqus Biochemistry and Molecular Biology* (Elsevier Science Publishing Co., Amsterdam (1988)) Vol. 19). Antibodies against NGF were used to render the bacteriophage non-infective. When NGF was added to the medium, T4-NGF was displaced from the antibody and was free to infect *Escherichia coli* (*E. coli*).

Bacteriophage T4 has also been used to detect antibodies against a wide range of compounds. For example, Becker et al. (*Immunochem.* (1970) 7:741) used a T4 bacteriophage to detect antibodies against p-azobenzenearsonate. Hurwitz et al. (*Eur. J. Biochem.* (1970) 17:273) used a bacteriophage to detect and estimate levels of angiotensin-II-beta-amide and its antibodies. Gurari et al. (*Eur. J. Biochem.* (1972) 26:247) used bacteriophage T4 in the detection of antibodies to nucleic acids. These detection methods involve the chemical modification of the T4 phage resulting in the non-specific exposure on the phage surface of a compound to which the antibodies to be assayed are targeted. Such antibodies render the bacteriophage non-infective, thus enabling the decrease in plaque formation to be used as a measure of the level of antibody present.

The T4 system has also been used to measure hapten concentrations (see, e.g., Hurwitz et al. (1970) *Eur. J. Biochem.* 17:273–277) In this system, T4 is chemically modified such that it exposes the desired hapten non-specifically on its surface. The addition of anti-hapten antibody destroys the infectivity of the phage. Infectivity is restored in the presence of hapten.

Although both the M13 and T4 phage systems can be used to detect the presence of a compound by their ability to become infected in the presence of that compound, infection by M13 is normally not immediately ascertainable, and T4 infection is lethal. Thus, these systems cannot be used where a quick screening or selection method based on the survival of the infected bacterial cell is desired, such as where a particular cell type is being selected, or when the object of phage infection is to restore the ability of an auxotrophic bacterial cell to survive on its own under a given set of growth conditions. Another limitation is that none of these methods of detection allow the in vitro assembly of phage, and none allow the display of non-proteinaceous target molecules on a particular area of a phage. Particular M13-derived phagemid systems,such as the one employed by Barbas et al. (*Proc. Natl. Acad. Sci,* USA (1991) 88:7978) do carry genes which would endow an infected cell with a selective growth advantage. However, these systems are limited to the expression of peptides or proteins. Furthermore, in all M13 systems where fusion proteins have been used to display proteins, the displayed protein has always been the molecule-of-interest and therefore not useful for the detection of such molecules.

Thus, what is needed are efficient and accurate assay methods utilizing bacteriophage infection that give fast results and that do not have to result in bacterial cell death. Additionally, assay methods utilizing bacteriophage infection are needed for non-proteinaceous molecules of interest and for living cells. In addition, novel selection and screening techniques are needed for the continuous production of desirable compounds by cell lines.

SUMMARY OF THE INVENTION

It has been discovered that a lambdoid bacteriophage having a target molecule chemically linked to one of its components, the gpV protein, can be successfully assembled in vitro such that the target molecule is displayed on the outer surface of the phage. Furthermore, this chemically modified lambdoid bacteriophage maintains its ability to infect *E coli*. These findings have been exploited to develop the present invention, namely, a method of detecting a molecule-of-interest in a solution, and a method of selecting or screening for cell lines which continuously produce desirable compounds, both utilizing a genetically and chemically modified lambdoid bacteriophage.

As used herein, the term "lambdoid bacteriophage" is meant to encompass all lambda-related phages and all derivatives, genetically engineered derivatives, and hybrids thereof, such as, but not limited to, Φ80, Φ81, phages 21, 82, 424, 432, λimm434, λimm21, phagemids, λEMBL, and λgt.

In this method, a protein construct is provided which includes a modified gpV protein. As used herein, the term "gpV protein" is meant to encompass any major tail protein found in the lambdoid bacteriophages such as, but not limited to, gpV protein, gpV-related proteins, and equivalents of lambdoid gpV protein in the tails of other lambdoid viruses.

The gpV protein is modified by the presence of a chemically reactive amino acid residue replacing a native gpV amino acid residue and which is chemically linked to the target molecule. Preferably, the chemically reactive amino acid residue is histidine (His), cysteine (Cys), tyrosine (Tyr), or tryptophan (Trp). Most preferably, the reactive amino acid residue is cysteine because it can be selectively modified. These reactive residues may be anywhere in the gpV amino acid sequence provided the modification does not interfere with gpV protein function or in phage assembly and structure. In one embodiment the, reactive residue is at the carboxy terminus of the gpV protein. In one preferred embodiment, the modified gpV protein has a cysteine residue instead of a serine residue at its carboxy terminus. The target molecule is chemically coupled to the chemically reactive amino acid residue either directly or via a chemical cross-linker such as a bifunctional cross-linking agent.

In preferred embodiments of the invention, the target molecule is a protein, peptide, glycoprotein, lipoprotein, hormone, proteoglycan, proteolipid, lipid, lipopolysaccharide, nucleic acid, cofactor, toxin, carbohydrate glycolipid, terpine, antibiotic, or vitamin. One preferred target molecule is a protein such as an enzyme, enzyme substrate, immunoglobulin, or binding portion thereof, ligand, toxin, growth factor, cytokine, receptor, or analog or fragment of any of these proteins.

The method of the invention includes assembling an infective lambdoid bacteriophage including the protein construct and having the target molecule displayed on the outer surface of the phage tail. In some embodiments, assembly is accomplished by providing the enzymes and components required for phage assembly in the form of a packaging extract obtained from an $E.\ coli$ cell infected with a mutant strain of lambdoid bacteriophage that requires exogenous gpV protein to assemble. As used herein, the term "packaging extract" includes at least that portion of the cytoplasm of the infected $E.\ coli$ cell which contains the enzymes and lambdoid components required for assembly.

The target molecule on the bacteriophage surface is then processed such that the phage is rendered reversibly non-infective or inactive. The term "reversibly non-infective" refers to the ability of the temporarily inactivated phage to become infective again. In some aspects of the invention, processing can be accomplished by treating the phage-linked target molecule with a binding molecule specific for the target molecule. In some embodiments, the binding molecule is an immunoglobulin, or binding portion thereof, specific for an antigenie determinant on the target molecule, a receptor specific for a ligand-type target molecule, a ligand which binds to a receptor-type target molecule, or a matrix to which the phage is immobilized via the target molecule. Immobilization renders the phage non-infective because it cannot bind to the lambda cell receptor.

The non-infective bacteriophage is then treated with a solution-to-be-tested which potentially contains the molecule-of-interest. Preferred solutions-to-be-tested include cell culture media, cell lysates, or biological samples such as blood, urine, serum, semen, or lacrimal secretions. The molecule-of-interest in the solution renders the non-infective bacteriophage infective again.

The term "molecule-of-interest" is meant to encompass any molecule whose activity or presence is desired, and which can directly or indirectly render the non-infective phage infective again. This may be a protein, peptide, hormone, nucleic acid, carbohydrate, lipid, glycoprotein, proteoglycan glycolipid, proteolipid, lipopolysaccharide, vitamin, toxin, terpene, antibiotic, or cofactor.

In some embodiments, the molecule-of-interest is a protein such as an enzyme, enzyme substrate, immunoglobulin, or binding portion thereof, ligand, toxin, growth factor, cytokine, receptor, or analog or fragment of any of these proteins. In some aspects of the invention, the molecule-of-interest is an enzyme which cleaves the target molecule. Cleavage of the binding molecule-linked target molecule liberates the bacteriophage, thereby rendering it infective once again. In other embodiments, the molecule-of-interest is an unbound target molecule. Unbound target molecules present in the solution-to-be-tested displace the binding molecule on the phage-linked target molecule and bind with the binding molecule, thereby liberating the phage and rendering it infective once again.

In another embodiment of the invention, the target molecule and the molecule-of-interest are the same and are ligands, and the binding molecule is a receptor specific for that ligand. In still another embodiment, the target molecule and the molecule-of-interest are the same and are receptors, and the binding molecule is a ligand that binds that receptor. In yet another embodiment, the molecule-of-interest is not identical to the target molecule, but yet is capable of binding to the binding molecule, thus displacing the target molecule. In another embodiment, the target molecule and the molecule-of-interest contain the same antigenic determinant, and the binding molecule is an immunoglobulin, or portion thereof, that binds that antigenic determinant. In yet another embodiment, the target molecule and the molecule-of-interest are the same immunoglobulin, or binding portion thereof, and the binding molecule contains an antigenic determinant bound by that immunoglobulin.

In the method of the invention, a bacterial cell such as an $E.\ coli$ cell is contacted with the treated bacteriophage for a time sufficient for the bacteriophage to infect the cell. Infected cells are then detected, infection being indicative of the presence of the molecule-of-interest in the solution.

In some embodiments, detection is accomplished by observing cell death in the form of cell lysis or plaque formation. Cell lysis results when the phage DNA successfully enters the cell, takes over the cell's protein synthetic operations, thereby directing it to produce viral components at the expense of cellular components and to assemble them into phage particles, and causes the cell to rupture or lyse such that the assembled viral particles are released. Plaques result when multiple neighboring cells plated on solid culture dishes lyse in this way, leaving clear or empty spots on the otherwise cloudy culture lawn.

Detection of infection is also accomplished by observing bacterial cell survival and/or growth in those embodiments of the invention where the bacterial cell infected by the treated phage is an auxotrophic mutant requiring a gene supplied by the phage. An example of one such gene is trpE carried by λEMBL3, a vector well known to those knowledgeable in the art, and where the phage is a mutant temperate phage such as one that is temperature sensitive for lysogeny.

As used herein, the term "temperate phage" refers to a phage that can be both lytic or lysogenic. A lysogenic phage integrates its nucleic acid into the host cell genome and remains quiescent, replicating only when the host genome replicates. In its lytic or vegetative phase, the phage nucleic acid excises itself from the host genome, or does not integrate itself into the host cell genome, and takes over the protein synthetic machinery of the cell at the expense of cellular components and causes phage progeny to be assembled. New phages are released from the cell when the cell lyses. A temperate phage may contain a mutation conferring temperature sensitivity, i.e., it is lysogenic only at low growth temperatures (e.g., about 32° C. and below) and is lytic at high growth temperatures (e.g., 37° C. and above, such as about 42° C.). Thus, at lower growth temperatures, lysogenic phage carrying a gene that will alleviate the auxotrophy of the cell integrates its DNA into the bacterial cell genome, providing it with the gene which the cell requires to survive.

Detection of infection is also accomplished by observing bacterial cell survival and/or growth in those embodiments of the invention where the phage, which is temperature sensitive as described in the above paragraph, carries a gene encoding antibiotic resistance. Infection of *E. coli* by this phage permits the cell to survive and grow on media containing the antibiotic whose resistance is encoded by the gene carried by the phage.

Bacterial cell growth is also indicative of phage infection, and hence, of the presence of the molecule-of-interest in the solution-to-be-tested, in embodiments where the bacterial cell to be infected is an auxotroph which itself is producing and secreting the molecule-of-interest, and where the molecule-of-interest and the target molecule are the same or are otherwise capable of displacing one another from the binding molecule. In this method, the target molecule is chemically linked to the gpV protein and assembled into an infective phage carrying a bacterial gene encoding a protein required by the auxotrophic bacterial cell for survival. The phage is then inactivated being bound by a binding molecule (such as an antibody directed to the target molecule), and then contacted with the solution-to-be-tested (e.g., the medium in which the mutant bacterial cell had been growing and/or with the bacterial cell, itself). If the solution contains unbound molecule-of-interest, or if the cell is producing and secreting the molecule-of-interest, the binding molecule bound to the phage linked target molecule will be displaced and instead will bind to the unbound molecule-of-interest in the solution. The liberated phage then infects the bacterial cell, and at lower growth temperatures (e.g., about 32° C.), provides it with the bacterial gene it needs for survival and growth.

In one aspect of the invention, a modified gpV protein is provided which encodes chemically reactive amino acid residues such as histidine, cysteine, tyrosine, and/or tryptophan. In another aspect, a nucleic acid is provided which encodes modified gpV protein. In yet other-aspects, the invention includes the protein construct including the modified gpV protein chemically linked via its chemically reactive amino acid residue to the target molecule.

In one embodiment the invention includes a genetically modified gpV protein having its carboxy terminal serine residue replaced with a chemically reactive amino acid residue such as cysteine. Preferably, this modified gpV protein has the amino acid sequence set forth in the Sequence Listing as SEQ ID NO:1.

Yet another embodiment of the invention is a chemically modified, infective lambdoid bacteriophage displaying the target molecule on its outer surface. In some aspects of the invention, this bacteriophage is assembled in vitro.

The target molecule-linked bacteriophage of the invention may be used in a method of selecting or enhancing the production of a molecule-of-interest, as described in copending U.S. patent application Ser. No. 991,115, now U.S. Pat. No. 5,348,882 herein incorporated by reference. This phage is a temperature sensitive lambdoid bacteriophage that carries a bacterial gene for a first compound in which nearby auxotrophic bacterial cells are deficient. These cells also overproduce a second compound and require a third compound for growth. In this method, a cell that is auxotrophic for a second compound and that overproduces a third compound, secretes a molecule-of-interest. This molecule-of-interest causes the phage to become infective by one of the aforementioned processes. The now infective phage then infects the bacterial cells that are deficient in the first compound. At growth temperatures at or below about 32° C., the phage is not lytic; rather, the nucleic acid of the phage integrates into the bacterial host cell genome, thereby converting the bacteria from an auxotroph to a prototroph for that first compound. A symbiotic relationship thus is established between the first cell (which overproduces the second compound and requires the third), and the second cell (which overproduces the third compound and requires the second compound and which also secretes a molecule-of-interest). This mutual crossfeeding enables the formation of a mixed colony.

In another embodiment, the bacteriophage carries a gene encoding drug resistance. The bacteria to be infected are not able to grow in the presence of the first compound which is an antibiotic. Infection by the bacteriophage restores the ability of the bacteria to grow in the presence of the first compound.

Other methods of selecting or screening for a cell producing a molecule-of-interest are also provided herein. In these methods, the protein construct of the invention is assembled with other viral components in vitro into an infective lambdoid bacteriophage displaying the target molecule on its outer surface. The target molecule is then processed such that the phage is rendered reversibly non-infective. A cell is contacted with the non-infective phage for a time sufficient to enable the molecule-of-interest produced by the cell to render the phage infective once again and then to enable the phage to infect the cell. Infection is detected, infection being indicative of the presence of a cell producing the molecule-of-interest.

In one aspect, the molecule-of-interest and the target molecule are the same. In another aspect, the phage assembled in vitro is a temperature sensitive lambdoid bacteriophage which also carries a gene encoding a cellular component. The cell, auxotrophic for the cellular component, is contacted at or below about 32° C. with the phage. At this low temperature, growth of the infective phage is detected as a measure of the presence of a cell producing the molecule-of-interest.

BRIEF DESCRIPTION OF THE DRAWINGS

The foregoing and other objects of the present invention, the various features thereof, as well as the invention itself may be more fully understood from the following description, when read together with the accompanying drawings in which.

DESCRIPTION OF THE PREFERRED EMBODIMENTS

It has been discovered that replacing an amino acid residue in the gpV protein with a chemically reactive amino acid residue and then chemically coupling this residue to a target molecule yields a protein construct that may successfully be assembled in vitro into an infective lambdoid bacteriophage having the target molecule displayed on the outer surface of its tail. Furthermore, a lambdoid phage modified in this manner still retains its ability to infect bacteria. Utilizing such a phage, a method of detecting a molecule-of-interest and of detecting a cell producing a molecule-of-interest have been developed. In these methods, either the death or growth of certain bacterial strains results from the presence of a molecule-of-interest depending on the nature of the infecting lambdoid bacteriophage genome and any specific needs of the infected bacteria.

Figure 1A:
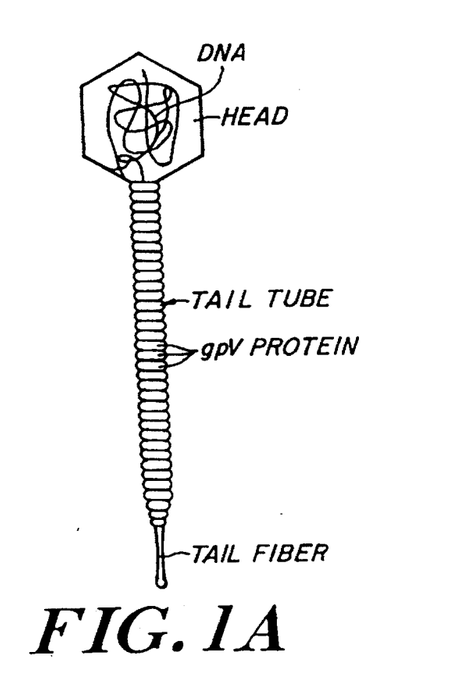
FIG. 1A is a diagrammatic representation of the bacteriophage lambda.

One type of lambdoid bacteriophage, the bacteriophage lambda, consists of a icosahedral head or capsid with a radius of 30 nm and a flexible tail 150 nm long ending in a tapered basal part and a single tail fiber (FIG. 1A). The genome of this bacteriophage is linear DNA. The DNA is found in the capsid head and has cohesive ends, the right one of which, as defined by the genetic map, protrudes into the upper third of the tail. The tail consists mainly of a tube of 32 disks of six gpV protein units, the product of the V gene.

Figure 1B:
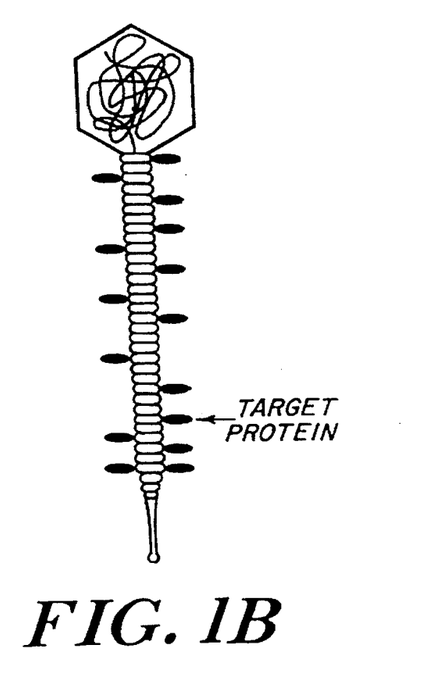
FIG. 1B is a diagrammatic representation of the chemically modified bacteriophage lambda of the invention.

In the present invention, the lambdoid bacteriophage is modified so as to expose or display a target molecule on the outer surface of its tail (FIG. 1B). This is accomplished by chemically linking the target molecule to a genetically modified gpV protein, thereby forming a protein construct, and then assembling the bacteriophage in vitro using this protein construct instead of or in combination with gpV protein.

Figure 2:
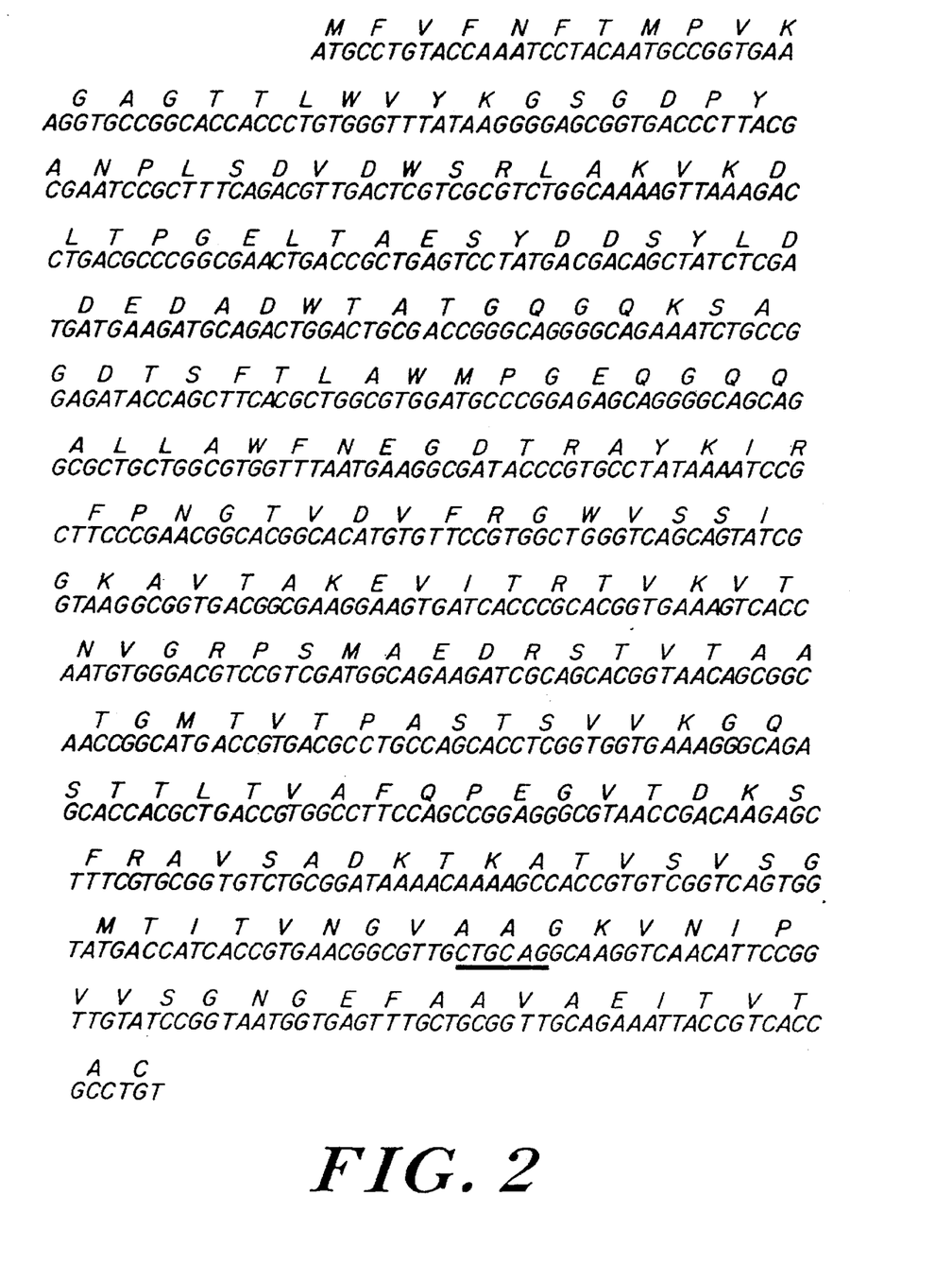
FIG. 2 is a schematic representation of the nucleic acid sequence and corresponding amino acid sequence of the modified gpV protein; (SEQ ID NOS. 1 and 2)

The protein construct is prepared from a genetically altered gpV protein having relatively non-reactive native amino acid residue(s) replaced with chemically reactive amino acid residues. Such chemically reactive amino acid residues include histidine, cysteine, tyrosine, and tryptophan. These reactive amino acid residues may be located anywhere throughout the sequence of the gpV protein and more than one amino acid residue may be replaced with such a reactive residue. Cysteine is the preferred reactive amino acid residue because there are no cysteine residues present in the native gpV protein sequence, and this residue can be selectively modified. The native sequence also contains no histidine residues, but does have five tyrosine residues and six tryptophan residues. For example, SEQ ID NO:1 in the Sequence Listing sets forth the amino acid sequence of a gpV protein in which the carboxy terminal serine residue at position 246 has been replaced with a cysteine residue (FIG. 2). This altered gpV protein can be prepared as follows.

The nucleic acid sequence of the V gene is known (Sanger et al. (1982) *J. Mol. Biol.* 162:729). This gene was simultaneously cloned and modified by PCR methods (Scarf, "Cloning with PCR" in *PCR Protocols. A Guide to Methods and Applications* (Innis et al., eds.) Academic Press, San Diego, Calif. (1990) pp.84–91), resulting in a full length V gene with its carboxy terminal Ser$^{246}$ codon replaced with a Cys codon TGT. The sequence for the modified V gene is set forth in the Sequence Listing as SEQ ID NO:2. The modified V gene has been cloned into an expression vector (pKK223-3, Pharmacia, Piscataway, N.J.) resulting in the pSYM1 plasmid shown in FIG. 4. This plasmid is used to transform *E. coli*. The transformed strain is induced (Sambrook et al. in *Molecular Cloning: A Laboratory Manual* (1989) p.17.13. Cold Spring Harbor Laboratory, Cold Spring Harbor, N.Y.), then lysed as a source of modified gpV protein. If necessary, the gpV protein can be purified further as described by Katsura et al. (*Virology* (1977) 76:129).

Partially purified, genetically modified gpV protein is then chemically coupled to a selected target molecule to form the protein construct. The target molecule can be any molecule that can be linked to the modified gpV protein via its reactive amino acid residue(s) without abolishing phage assembly or infectivity. Such target molecules include proteins, peptides, carbohydrates, hormones, glycoproteins, proteoglycans, lipoproteins, proteolipids, lipids, lipopolysaccharides, toxins, cofactors, nucleic acids, glycolipids, terpenes, antibiotics, or vitamins. Useful target proteins include immunoglobulins or portions thereof (such as Fab, Fv, (Fab')$_2$), receptors or portions thereof (such as the estrogen receptor and the insulin receptor), ligands (such as ciliary neurotrophic factor and luteinizing hormone), enzymes (such as beta-lactamase, triose phosphate isomerase, and hexokinase), enzyme substrates (such as pre-interleukin-1, proinsulin, and erythropoietin), cytokines (such as macrophage migration inhibition factor and the interleukins), growth factors (such as fibroblast growth factor and granulocyte colony stimulating factor), or toxins (such as pertussis toxin and botulinum toxin A).

Coupling of the target molecule to the gpV protein may be accomplished by any chemical linkage method known in the art, such as covalent bonding. For example, the sulfhydryl group in a cysteine residue of the gpV protein and a sulfhydryl group in any cysteine residues present in the target molecule may be oxidized to form a disulfide bond between them. The target molecule instead can be chemically reacted with the imidazolyl group in histidine, the hydroxyl group in tyrosine, or the indoyl group in tryptophan.

The target molecule may be chemically cross-linked to the reactive amino acid residue of the gpV protein. Cross-linking can be accomplished using any number of known cross-linking reagents, such as those set forth in U.S. Pat. No. 5,112,615, herein incorporated by reference. One type of useful cross-linking reagent is a bifunctional reagent such as β-maleimidopropionic acid N-hydroxysuccinimide ester which can be employed according to methods known in the art (e.g., *Laboratory Techniques in Biochemistry and Molecular Biology*, Elsevier Science Pub. Co., Amsterdam (1988) vol. 19).

To obtain the bacteriophage of the invention, the protein construct is contacted with other lambdoid phage components and enzymes required to assemble the phage in vivo. Methods of phage assembly are well known in the art (see, e.g., Hohn (1979) *Meth. Enzymol.* 68:299–309). In vitro assembly enables the ratio of unmodified gpV protein to modified gpV protein to be controlled, thus allowing the introduction of a limited number of protein constructs per phage particle.

Lambdoid components and assembly enzymes can be provided in the form of a cell lysate (or packaging extract) from *E. coli* preinfected with lambdoid phage that is defective in a step of morphogenesis. For example, when bacteria infected with a prophage mutant in gene V are induced, precursor phage particles accumulate. Induction may be accomplished by a shift in temperature if the infecting phage has a temperature sensitive genotype such as λV⁻ C1ts Sam7. To obtain a V⁻ derivative of a commercially available lambda phage, such as λC1857Sam7 (New England Biolabs, Beverly, Mass.), the phage are mutagenized (Katsura (1976) *Molec. Gen. Genet.* 148:31). *E. coli* JM105 (Stratagens, La Jolla, Calif.) carrying the pSYM1 plasmid are infected with the mutagenized phage population. Colonies appearing at 32° C. are replica plated to plates with or without IPTG, which induces gpV production. Colonies which grow on plates without IPTG, but do not grow on plates with IPTG, are selected as a source of V⁻ phage. The V gene mutation can be complemented by the addition of the missing gpV protein, which, in this invention, is chemically coupled to a target protein.

The assembled phage is then rendered non-infective. This may be accomplished by the addition of a binding molecule which is directed to the target molecule on the bacteriophage. Useful binding molecules include antibodies or, binding portions thereof such as Fv, Fab, or (Fab')₂ fragments. The production of such antibodies and biochemically or genetically produced fragments is well known in the art (see, e.g., *Antibodies: A Laboratory Manual* (Harlow and Lane, eds.) Cold Spring Harbor Laboratory, Cold Spring Harbor, N.Y. 1988).

Other useful binding molecules include receptors and ligands. When the target molecule is a receptor ligand, the receptor serves as an immobilizing agent. Receptors as binding molecules may be presented in micelles or liposomes or on cell surfaces to keep their configuration. Such receptor-containing liposomes can be prepared using the method of Georgoussi et al. (*Biochem. Biophys. Acta* (1990) 1055:69). Receptors which can be presented to the phage in this way include, but are not limited to, the nicotinic acetylcholine receptor (Chak et al. (1992) *Meth. Enzymol.* 207:546), the inositol 1,4,5-triphosphate receptor (Kamata et al. (1992) *J. Biochem.* 111:546), the hepatic vasopressin receptor (Georgoussi, ibid.) and the rat ovarian receptor for luteinizing hormone (Kusada et al. (1986) *J. Biol. Chem.* 261:16161). Ligands include all molecules capable of binding to the target molecule in a competitive fashion. When ligands are used as the binding molecule, they must be immobilized as described below.

Other useful binding molecules are enzyme substrates such as acetylcholine, γ-amino butyricacid, insulin, and glucagon.

Alternatively, the phage can be rendered non-infective by immobilization to a binding molecule such as a matrix via linkage to the target molecule. Such matrices include, but are not limited to, commercially available materials such as a gel consisting of dextran cross-linked with epichlorohydrin (Sephadex™) a special gel prepared from agarose (Sepharose™), and agarose. When the phage is immobilized to a matrix it is unable to bind to and infect a cell. Immobilization to the matrix may be accomplished by chemical linkage such as one employing various chemical cross-linking methods (see, e.g. Wilchek et al. (1984) *Meth. Enzymol.* 104:3; and U.S. Pat. No. 5,112,615, herein incorporated by reference).

Figure 5A:
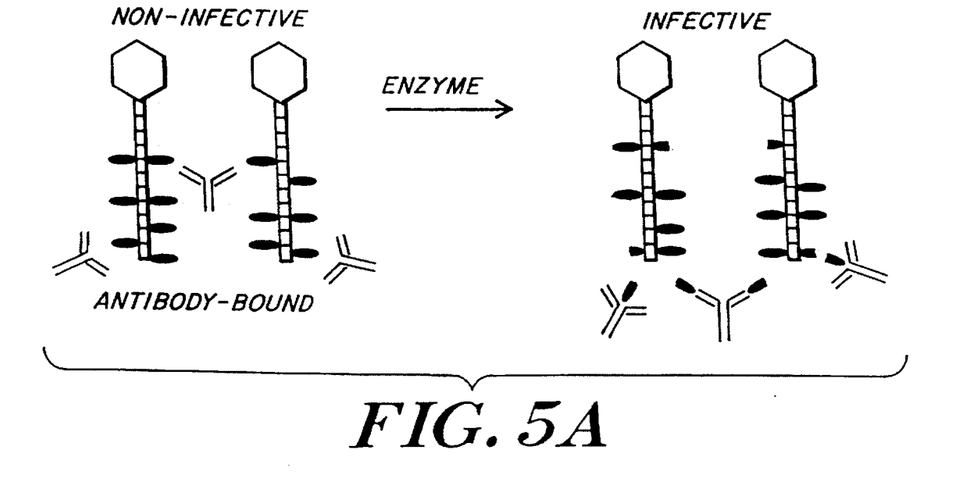
FIGS. 5A–5C are diagrammatic illustrations of several of embodiments of the method of the invention.
Figure 5B:
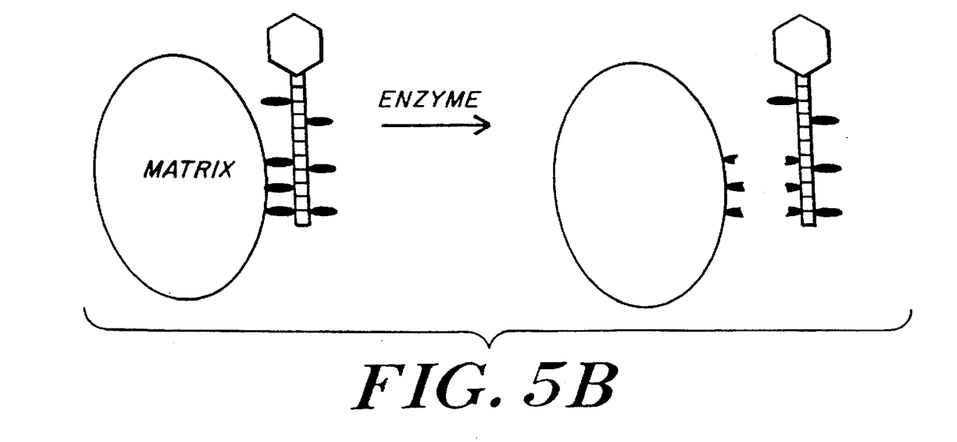
Figure 5C:
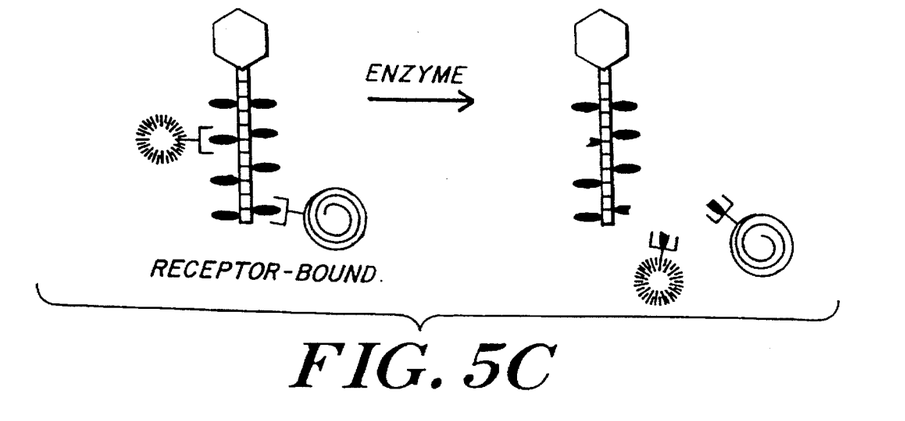

The method of the invention may be designed such that the immobilized or inactivated phage is released or liberated from the matrix or binding molecule by the molecule-of-interest. In this way, the presence of the molecule-of-interest can be determined and quantitated by the relative activity of the phage. For example, if the molecule-of-interest is an enzyme capable of cleaving the target molecule, the phage is rendered infective once again upon its liberation from the binding molecule (FIGS. 5A–5C). The target molecule may have an antigenic determinant recognized by an antibody (FIG. 5A), be a ligand which is bound to a matrix (FIG. 5B), or be a ligand which binds a receptor (FIG. 5C). Any enzyme which cleaves the target molecule releases the phage which is now infective. The ability of these phage to infect bacteria is then assayed, for example, using the plate method of Davis et al. (in *Advanced Bacterial Genetics* (1980) Cold Spring Harbor Laboratory, Cold Spring Harbor, N.Y., p. 71).

Figure 6A:
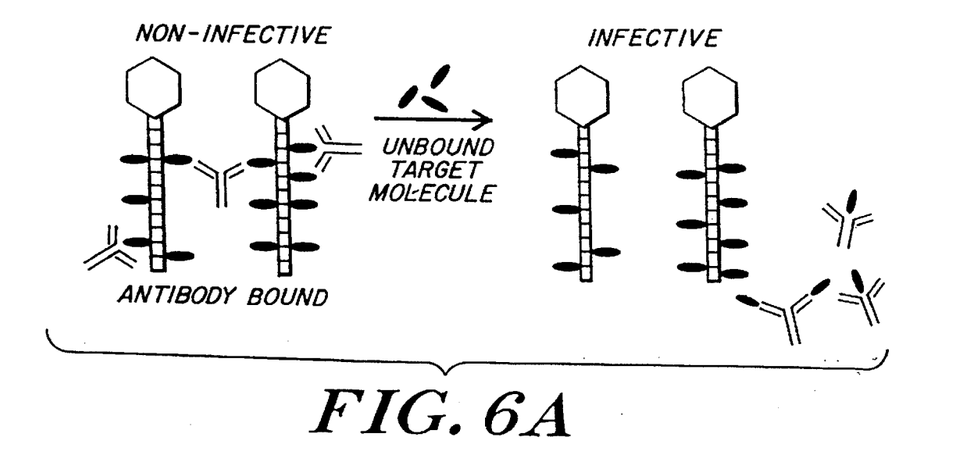
FIGS. 6A and 6B are diagrammatic illustrations of other embodiments of the method of the invention.
Figure 6B:
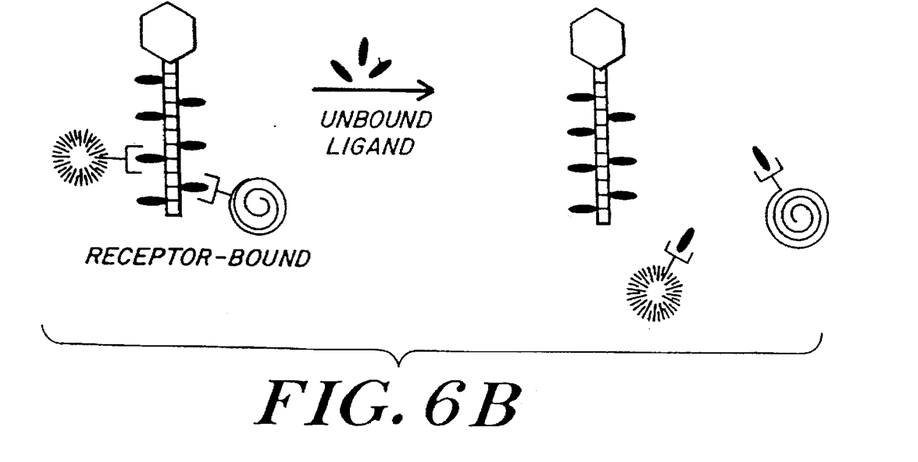

If the molecule-of-interest has an antigenic determinant which the antibody molecule bound to the target molecule recognizes, the method is performed as delineated in FIGS. 6A or 6B. The bound target molecule (and hence the inactivated phage) is liberated by the presence of unbound molecule-of-interest in the solution which competes for the binding molecule. If the binding molecule is a receptor which loses its three-dimensional conformation upon purification, it may have to be presented on a liposome, micelle, or on the surface of a cell.

The method of the invention can also be used to select a cell type that produces a desired product, such as a ligand or modified enzyme, from a population that does not produce that product. For example, in an in vitro assembly reaction partially purified, genetically modified gpV protein cross-linked to a target molecule is contacted with the cell extract from an *E. coli* previously infected with a phage, such as λC1857 V⁻trpE⁺, obtained as described above. Either an antibody directed against the target molecule, or a ligand which can bind the receptor, or a cell receptor specific for the target molecule is utilized to render the modified bacteriophage non-infective, or if the molecule-of-interest is an enzyme which cleaves its substrate, the target molecule can be chemically linked to a matrix, as described above.

A library that consists of a mutagenized population of a cloned enzyme or, antibody is transformed in an *E. coli* strain which is defective in the marker gene carried by the bacteriophage. By "cloned enzyme or antibody" is meant the enzyme or antibody which is produced by expression of the cloned gene encoding the enzyme or antibody. The cloned enzyme or antibody gene can be mutagenized by one of a variety of methods such as those described by. Foster (*Meth. Enzymol.* (1991) 204:114). The cloned enzyme or antibody also must be excreted into the surrounding media. Several methods by which cloned enzymes are excreted are provided in the scientific literature (e.g., Chalmers et al. (1990) *Appl. Environ. Microbiol.* 56:104; Lazzaroni et al. (1981) *J. Bacteriol.* 145:1351; and Rampf et al. (1991) *FEBS Lett.* 280:27), as are methods by which cloned antibody fragments are excreted (e.g., Ward et al. (1989) *Nature* 341:544).

In the case where mutagenized enzyme is employed, the target molecule is an analog of the natural substrate for the enzyme. This analog is not cleaved by the wild type enzyme, but if a mutagenized enzyme present in the mutant library is capable of cleaving the analog, phage are released and infect the cell excreting the enzyme with the modified specificity thus permitting the cell to grow.

In the case where mutagenized antibody is employed, the target molecule contains the epitope or antigenic determinant for the antibody. Although antibodies do not normally cleave their antigen, a mutagenized antibody present in the mutant library may be capable of cleaving the antigen. If so, phage are released and infect the cell excreting the antibody with the modified activity, thus permitting the cell to grow. If the immobilizing agent is an antibody, it must recognize a different epitope on the antigen and must not interfere with the binding of the excreted antibody.

The method of the invention offers several advantages over other systems employing bacteriophages such as M13 or T4. First, lambdoid bacteriophage can be assembled in vitro, and thus the target molecule does not have to be a protein or peptide. In fact, any molecule that can be linked to the gpV protein can be employed as long as it does not completely interfere with in vitro assembly or the ability of the resulting bacteriophage to infect bacteria.

Second, the method does not have to result in the death of the infected bacteria. Rather, it can be used to isolate cells that excrete/secrete a desired compound, unlike the M13 and T4 systems. By using a temperature sensitive strain of lambdoid bacteriophage and a bacterial cell population that requires for growth a particular gene product supplied by the bacteriophage, those cells that excrete/secrete the desired compound will render infective an inactivated bacteriophage lambda which, in turn, will infect the cell, and at lower temperatures enable the cell to grow. Likewise, the method can be used to isolate either a bacterial mutant or a genetically engineered bacteria that excretes or secretes a molecule-of-interest from a population of non-excretors.

Third, this method enables the selective modification of a specific protein, and hence the selective display of a target molecule, unlike the T4 system. With non-specific modifications, a large percentage of the modified phages are rendered permanently non-infective. For example, when nerve growth factor (NGF) was coupled to bacteriophage T4, 76% of the phage were rendered non-infective (Oger et al. (1974) *Proc. Natl. Acad. Sci. (USA)* 71:1554–1558).

Fourth, as an extension of the method described in the previous paragraph, the method can also be used to screen enzyme libraries for clones having the ability to cleave altered substrate. Immobilization of the bacteriophage via the altered substrate enables isolation of strains from a library that contain an enzyme with the altered specificity from the library.

Fifth, by coupling the lambdoid phage technology described herein with the previously described symbiotic screening method (U.S. patent application Ser. No. 991,115) the range of compounds that can be screened is greatly increased; the desired compound no longer has to be required for the growth of one of the strains employed in the symbiosis. Desired compounds can be expanded to include all molecules which meet the criteria as set forth in the lambdoid phage system described herein.

The following examples illustrate the preferred mode of making and practicing the present invention, but is not meant to limit the scope of the invention since alternative methods may be utilized to obtain similar results.

EXAMPLES

1. Preparation of Modified V Gene and Its Expression

Figure 4:
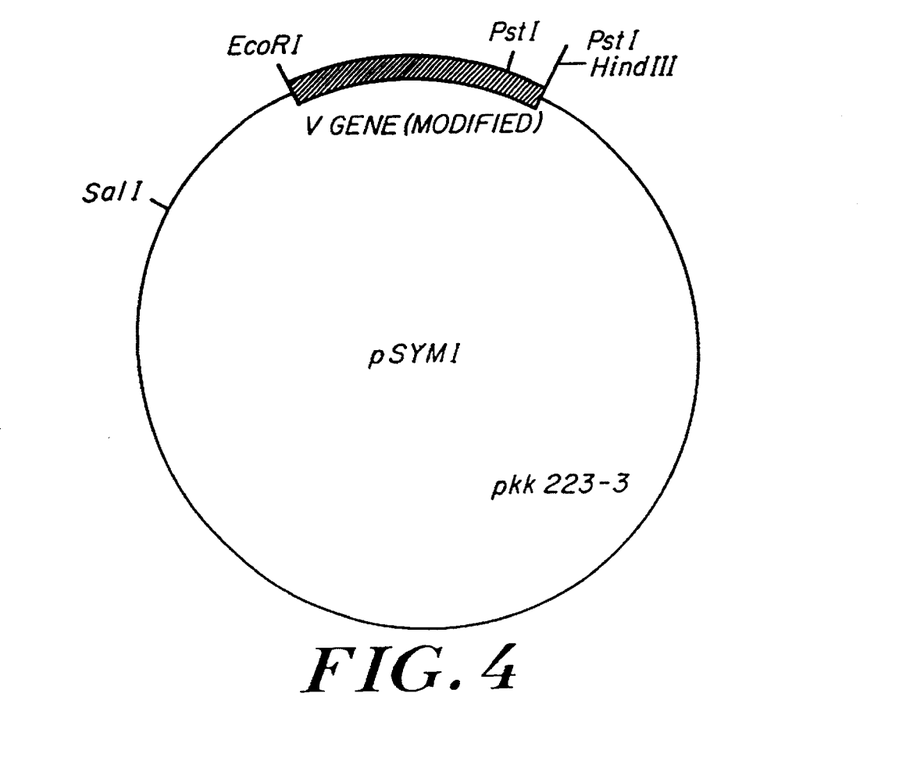
FIG. 4 is a schematic representation of the pSYM1 plasmid which contains the gene encoding the modified gpV protein of the invention.

The V gene is simultaneously cloned into the expression vector pkk223-3 (Pharmacia, Piscataway, N.J.) and modified using the PCR protocol of Scharf ("Cloning with PCR" in *PCR Protocols. A Guide to Method and Applications* (Innis et al., eds.) Academic Press, San Diego, Calif. (1990) pp. 84–91). The resulting plasmid is shown in FIG. 4 (pSYM1).

Figure 3:
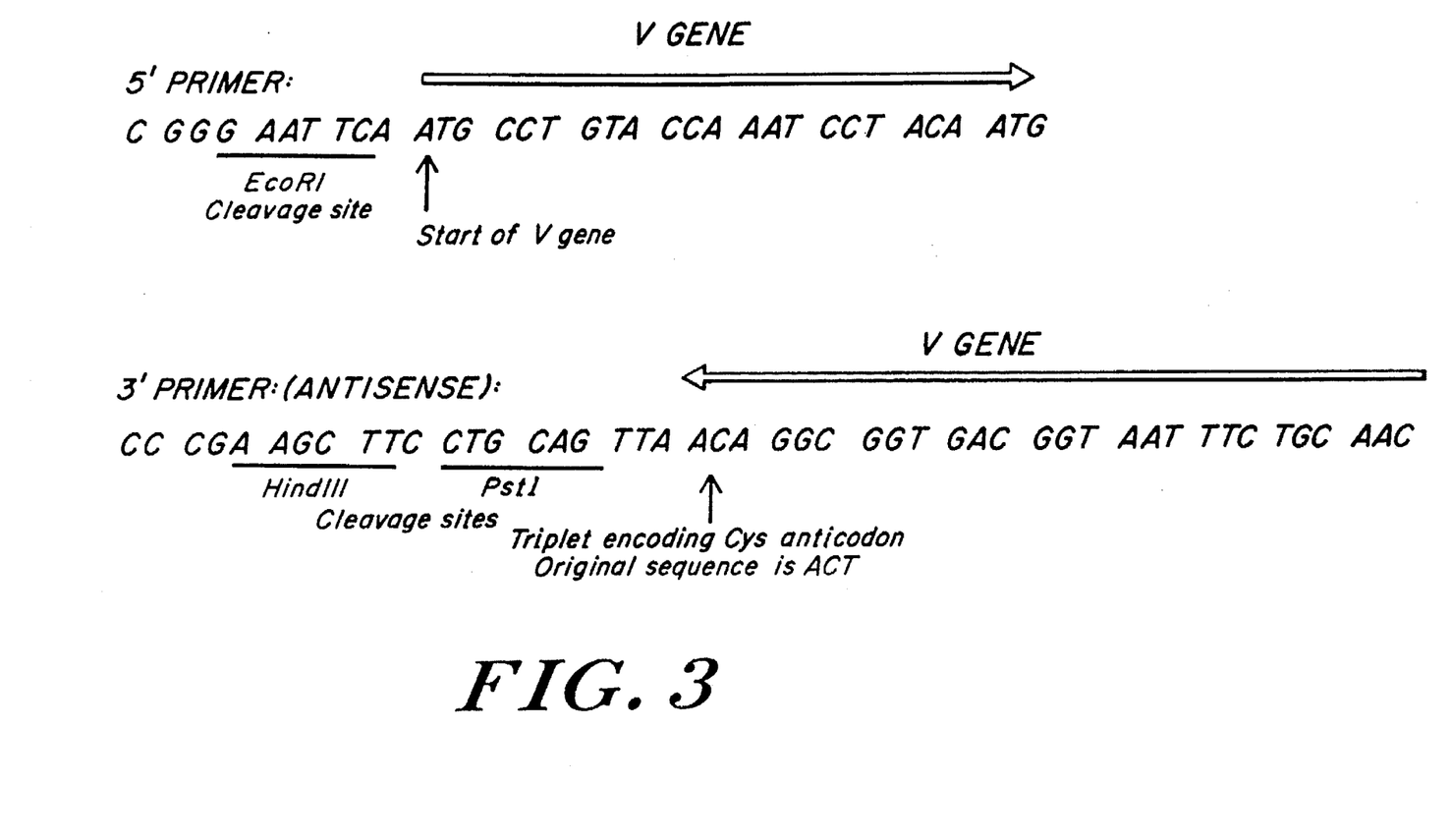
FIG. 3 is a schematic representation of the 3' and 5' primers used to provide the PCR fragment containing the full length, modified V gene fragment; (SEQ ID NOS. 3 and 4)

The primers used for the procedure are shown in FIG. 3 and are set forth in the Sequence Listing as SEQ ID NOS:3 and 4. The primer that anneals to the 5' end of the V gene (SEQ ID NO:3) is designed to include an EcoRI restriction endonuclease cleavage site. The primer that anneals to the 3' end of the V gene (SEQ ID NO:4) is designed to include HindIII and PstI restriction endonuclease cleavage sites. In addition, this primer contains a single base substitution in the last codon of the V gene. This substitution results in the conversion of $Ser^{246}$ to $Cys^{246}$.

The plasmid is then used to transform *E. coli* strain JM109 (Yanish-Perron et al. (1985) *Gene* 33:103) and then induced to express the modified gpV protein by addition of IPTG (Sambrook et al. (1989) *Molecular Cloning: A Laboratory Manual* p.17.13, Cold Spring Harbor Laboratory, Cold Spring Harbor, N.Y.). Cell extracts prepared by sonication serve as a source of modified gpV protein. If necessary, modified gpV is further purified according to Katsura et al. (*Virol.* (1977) 76:129).

2. Preparation of Antibody Column

A column having antibodies directed to the target molecule of the V-gene protein construct is prepared essentially as described in *Antibodies: A Laboratory Manual* ((Harlow and Lane, eds.) Cold Spring Harbor Laboratory, Cold Spring Harbor, N.Y., (1988)). Briefly, specific antibodies are mixed with protein A beads (Sigma Chemical Company, St. Louis, Mo.) using 2 mg of antibody per milliliter of beads. The bead solution is mixed gently for 1 hour at room temperature. The beads are then washed and chemically cross-linked to the antibodies using a bifunctional cross-linking reagent such as dimethylpimelimidate (Sigma Chemical Company). Chemical cross-linking is accomplished by shaking the antibody-coated beads for 30 minutes in the presence of 20 mM dimethylpimelimidate. The cross-linking reaction is stopped by washing the beads in 0.2M ethanolamine followed by a 2 hour incubation at room temperature in 0.2M ethanolamine.

3. Detection of Ciliary Neurotrophic Factor

Rabbit ciliary neurotrophic factor (CNTF) is isolated from rabbit sciatic nerves as described by Lin et al. (*Science* (1989) 246: 1023–1025). The CNTF is chemically cross-linked though a cysteine residue to the sole cysteine residue at the carboxy terminus of the modified gpV protein using 4-maleimidobenzophenone (Tao et al. (1986) *Biochemistry* 25:7633–7639). An in vitro lambda packaging extract is prepared from *E. coli* carrying the $\lambda C1_{ts}$ $V^-$ temperature sensitive genotype (Hohn (1979) *Meth. Enzymol.* 68:299–309). The CNTF-gpV protein construct is added to the packaging extract followed by the addition of unmodified gpV protein. The resulting in vitro-assembled phage containing CNTF exposed on their tail are purified by running the reaction mixture over an anti-CNTF antibody column, prepared as described above. Antibodies to CNTF are prepared as described by Lin et al. (ibid.). The CNTF-modified phage is inactivated using anti-CNTF antibodies, as described by Hurwitz et al. (*Eur. J. Biochem.* (1970) 17:273). The appropriate ratio of modified phage to antibody is determined experimentally using the method of Oger et al. (*Proc. Natl. Acad. Sci. (USA)* (1974) 71:1554). Inactivated phage are incubated with cell extracts suspected of containing CNTF (the solution-to-be-tested) under the conditions described by Olger et al. (ibid.). The infectivity of the phage is then assayed using the plate method of Davis et al. (in *Advanced Bacterial Genetics*, Cold Spring Harbor Laboratory, Cold Spring Harbor, N.Y. (1980) p. 71). The increase in the number of infective phage is directly proportional to the amount of CNTF present in the original sample.

4. Detection of Interleukin-1β Converting Enzyme

The precursor form of interleukin-1β (pIL-1β) has been cloned into *E. coli* (March et al. (1985) *Nature* 315:641–647). This precursor is isolated from the *E. coli*, using the method of Black et al. (*J. Biol. Chem.* (1988) 263:9437) and chemically cross-linked, through one of its cysteine residues, to the cysteine residue of the modified gpV, as described above. An in vitro lambda packaging extract is made from *E. coli* carrying λCIts V⁻, as described above. The pIL-1β-gpV protein construct is added to the packaging extract followed by the addition of unmodified gpV protein. The resulting in vitro assembled phage containing pIL-1β are purified by running the reaction mixture over an anti-IL-1β antibody column prepared as described above. Antibodies to IL-1β are obtained as described by Lin et al. (ibid.) using a synthetic peptide which spans $Cys^{124}$. Phage that bind antibodies to this region will most likely have pIL-1β cross-linked to modified gpV at a cysteine residue other than $Cys^{124}$. This is important because $Cys^{124}$ is located near the ICE cleavage site and cross-linking through this residue is likely to interfere with ICE activity. The pIL-1β-modified phage are inactivated by cross-linking and thus immobilizing them to agarose (Wilchek et al. (1984) *Meth. Enzymol.* 104:3). The immobilized phage are then incubated with media suspected of containing IL-1β converting enzyme (ICE) under the conditions described by Oger et al. (*Proc. Natl. Acad. Sci.* (USA) (1974) 71:1554). The infectivity of the phage is assayed using the plate method of Davis et al. (in *Advanced Bacterial Genetics*, Cold Spring Harbor Laboratory, Cold Spring Harbor, N.Y. (1980) p.71). The increase in the number of infective phage is directly proportional to the amount of ICE present in the original sample.

5. Selection of *E. coli* Secreting Antibodies Capable of Cleaving Granulocyte Colony Stimulating Factor (G-CSF)

The Fv fragment of antibodies is the minimal structure for antigen-binding activity (Pluckthun et al. (1989) *Meth. Enzymol.* 178:497). The nucleotide sequence encoding the light chain variable region ($V_L$) and the heavy chain variable regions ($V_H$) of a murine antibody raised against G-CSF (Sigma Chemical Co., St. Louis, Mo.) are cloned using PCR as described by Chaudhary et al. (*Proc. Natl. Acad. Sci.* (USA) (1990) 87:1066). A hybridoma cell line producing monoclonal antibodies against G-CSF is prepared as described by Harlow and Lane (in *Antibodies: A Laboratory Manual*, Cold Spring Harbor Laboratory, Cold Spring Harbor, N.Y. (1988) pp. 139–243). The $V_L$ and $V_H$ regions are cloned in the expression vector pASK22 (Pluckthun et al., ibid.). G-CSF is chemically cross-linked to the cysteine residue of the modified gpV, as described above. An in vitro lambdoid packaging extract is made from *E. coli* carrying λCIts V⁻ trpE⁺, as described above. G-CSF-gpV is added to the packaging extract followed by the addition of gpV. The resulting in vitro assembled phage containing G-CSF are purified by running the reaction mixture over an anti-G-CSF antibody column, prepared as described above. The G-CSF-modified phage are inactivated by cross-linking to the agarose as previously described. Immobilized (inactivated) phage are incubated with *E. Coli* Sym3 (λ⁻, F⁺ ΔtrpE recA hflA) that have been transformed with a library consisting of a mutagenized population of the cloned antibody fragments. The cloned antibody fragments can be mutagenized by one of a variety of methods such as those described by Foster (*Meth. Enzymol.* (1991) 204:114). The transformed cells are plated on supplemented Davis minimal media lacking tryptophan (*Difco Manual*, 10th Edition. Difco Laboratories, Detroit, Mich. (1984) p. 572). Because *E. coli* Sym3 requires tryptophan for growth, it will grow poorly unless infected by a lambdoid bacteriophage carrying trpE+ which restores growth of *E. coli* Sym3 on medium lacking tryptophan. Therefore, a transformant of *E. coli* Sym3 that secretes an antibody fragment capable of cleaving G-CSF releases nearby lambdoid bacteriophage which will infect the cell, resulting in a great enhancement of the infected cell's growth rate relative to other cells on the plate. This cell gives rise to a visible colony. A second round of screening permits isolation of the strain producing the desired molecule-of-interest.

6. Detection of Genetically Engineered *Saccharomyces cerevisiae* Strains Overproducing Erythropoietin Erythropoietin (EPO) (Sigma Chemical Company, St. Louis, Mo.), is chemically cross-linked to the cysteine residue of the modified gpV, as described above. An in vitro lambdoid packaging extract is made from *E. coli* carrying λCIts V⁻ trpE⁺, as described above. The EPO-gpV protein construct is added to the packaging extract followed by the addition of gpV. The resulting in vitro assembled phage containing EPO are purified by running the reaction mixture over an anti-EPO antibody column, as described above. Antibodies are prepared as described in the previous example. The EPO-modified phage are immobilized by cross-linking them to agarose as previously described. A mouse kidney cDNA library present in the yeast vector pYEUra3 is cloned into *S. cerevisiae* (American Type Culture Collection No. ATCC #20169) containing a deletion in a portion of the *THR4* gene. The cloned library may be prepared using methods well known in the art, or is commercially available (e.g., Clontech Laboratories, Palo Alto, Calif.). *E. coli* (American Type Culture Collection No. ATCC #21277) which excrete threonine and require proline for growth, are P1-transduced with a lysate prepared from an *E. coli* strain PLK831t(ΔtrpE, pyrF::Tn5) which is auxotrophic for tryptophan. PLK831t is a kanamycin resistant, P1 transductant of PLK831 (*E. coli*, Genetic Stock Center, Yale University, New Haven, Conn.) and the P1 lysate was prepared from *E. coli* carrying PyrF::Tn5 (Shaw et al. (1979) *Genetics* 92:741). The resultant strain is then P1-transduced with a lysate prepared from *E. coli* Y1089 which carries hflA::Tn10 (Stratagene, La Jolla, Calif.). The resulting tetracycline-resistant strain is designated *E. coli* Sym6. Approximately $10^7$ cells of the resulting *S. cerevisiae* are mixed with $10^8$ *E. coli* Sym6 and the experimentally determined amount of immobilized phage. The mixture is plated on minimal media lacking proline, threonine, and tryptophan (0.67% yeast nitrogen base without amino acids (Difco Laboratories, Detroit, Mich.), 2% dextrose, 1.5% agar, pH 6.3) plus isoleucine and methionine, both present at 40 mg/liter. Cells of *S. cerevisiae* which also secrete EPO release phage (carrying a trp gene) that infect nearby *E. coli*, thus allowing the infected *E. coli* to grow in the absence of tryptophan. The infected *E. coli* grow in a symbiotic relationship with the *S. cerevisiae* cells that secrete EPO, resulting in the formation of a mixed colony. The *S. cerevisiae* is purified on the minimal media plus threonine because the *E. coli* can not grow without additional supplements.

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An infective bacteriophage lambda comprising a head and a tail, the tail having on its outer surface a modified gpV protein, the modified gpV protein having the sequence set forth in SEQ ID NO:1, wherein a chemically reactive amino acid residue selected from the group consisting of histidine, cysteine, tryptophan, and tyrosine is substituted at amino acid position 246, and wherein the tail has a proteinaceous target molecule chemically coupled to said chemically reactive amine acid residue.

2. The infective bacteriophage lambda of claim 1 wherein the chemically reactive amino acid residue is cysteine.

3. The infective bacteriophage lambda of claim 1 wherein the target molecule is selected from the group consisting of a lipoprotein and a glycoprotein.

4. The infective bacteriophage lambda of claim 1 wherein the target molecule is a protein selected from the group consisting of an enzyme, enzyme substrate, immunoglobulin, ligand, toxin, growth factor, cytokine, hormone, and receptor.

5. The infective bacteriophage lambda of claim 1 wherein the target molecule is chemically coupled to the amino acid residue by means of a cross-linking reagent.

* * * * *

UNITED STATES PATENT AND TRADEMARK OFFICE
CERTIFICATE OF CORRECTION

PATENT NO. : 5,663,069
DATED : September 2, 1997
INVENTOR(S) : Bryan L. Ray et al.

It is certified that error appears in the above-indentified patent and that said Letters Patent is hereby corrected as shown below:

In claim 1, line 25, after "tive", "amine" should be changed to --amino--.

Signed and Sealed this

Eleventh Day of November, 1997

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 246 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( x i ) SEQUENCE DESCRIPTION: SEQ ID NO:1:

```
Met Pro Val Pro Asn Pro Thr Met Pro Val Lys Gly Ala Gly Thr Thr
  1               5                  10                  15

Leu Trp Val Tyr Lys Gly Ser Gly Asp Pro Tyr Ala Asn Pro Leu Ser
             20                  25                  30

Asp Val Asp Trp Ser Arg Leu Ala Lys Val Lys Asp Leu Thr Pro Gly
         35                  40                  45

Glu Leu Thr Ala Glu Ser Tyr Asp Asp Ser Tyr Leu Asp Asp Glu Asp
     50                  55                  60

Ala Asp Trp Thr Ala Thr Gly Gln Gly Gln Lys Ser Ala Gly Asp Thr
 65                  70                  75                  80

Ser Phe Thr Leu Ala Trp Met Pro Gly Glu Gln Gly Gln Gln Ala Leu
                 85                  90                  95

Leu Ala Trp Phe Asn Glu Gly Asp Thr Arg Ala Tyr Lys Ile Arg Phe
                100                 105                 110

Pro Asn Gly Thr Val Asp Val Phe Arg Gly Trp Val Ser Ser Ile Gly
             115                 120                 125

Lys Ala Val Thr Ala Lys Glu Val Ile Thr Arg Thr Val Lys Val Thr
         130                 135                 140

Asn Val Gly Arg Pro Ser Met Ala Glu Asp Arg Ser Thr Val Thr Ala
145                 150                 155                 160

Ala Thr Gly Met Thr Val Thr Pro Ala Ser Thr Ser Val Val Lys Gly
                 165                 170                 175

Gln Ser Thr Thr Leu Thr Val Ala Phe Gln Pro Glu Gly Val Thr Asp
             180                 185                 190

Lys Ser Phe Arg Ala Val Ser Ala Asp Lys Thr Lys Ala Thr Val Ser
         195                 200                 205

Val Ser Gly Met Thr Ile Thr Val Asn Gly Val Ala Ala Gly Lys Val
     210                 215                 220

Asn Ile Pro Val Val Ser Gly Asn Gly Glu Phe Ala Ala Val Ala Glu
225                 230                 235                 240
```

```
        Ile  Thr  Val  Thr  Ala  Cys
                            245
```

( 2 ) INFORMATION FOR SEQ ID NO:2:

( i ) SEQUENCE CHARACTERISTICS:
        ( A ) LENGTH: 741 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:2:

```
ATGCCTGTAC  CAAATCCTAC  AATGCCGGTG  AAAGGTGCCG  GGACCACCCT  GTGGGTTTAT    60
AAGGGGAGCG  GTGACCCTTA  CGCGAATCCG  CTTTCAGACG  TTGACTGGTC  GCGTCTGGCA   120
AAAGTTAAAG  ACCTGACGCC  CGGCGAACTG  ACCGCTGAGT  CCTATGACGA  CAGCTATCTC   180
GATGATGAAG  ATGCAGACTG  GACTGCGACC  GGGCAGGGGC  AGAAATCTGC  CGGAGATACC   240
AGCTTCACGC  TGGCGTGGAT  GCCCGGAGAG  CAGGGGCAGC  AGGCGCTGCT  GGCGTGGTTT   300
AATGAAGGCG  ATACCCGTGC  CTATAAAATC  CGCTTCCCGA  ACGGCACGGT  CGATGTGTTC   360
CGTGGCTGGG  TCAGCAGTAT  CGGTAAGGCG  GTGACGGCGA  AGGAAGTGAT  CACCCGCACG   420
GTGAAAGTCA  CCAATGTGGG  ACGTCCGTCG  ATGGCAGAAG  ATCGCAGCAC  GGTAACAGCG   480
GCAACCGGCA  TGACCGTGAC  GCCTGCCAGC  ACCTCGGTGG  TGAAAGGGCA  GAGCACCACG   540
CTGACCGTGG  CCTTCCAGCC  GGAGGGCGTA  ACCGACAAGA  GCTTCGTGC   GGTGTCTGCG   600
GATAAAACAA  AAGCCACCGT  GTCGGTCAGT  GGTATGACCA  TCACCGTGAA  CGGCGTTGCT   660
GCAGGCAAGG  TCAACATTCC  GGTTGTATCC  GGTAATGGTG  AGTTTGCTGC  GGTTGCAGAA   720
ATTACCGTCA  CCGCCTGTTA  A                                                741
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear     ( i i ) MOLECULE TYPE: cDNA (genomic)

( i i i ) HYPOTHETICAL: NO

( i v ) ANTI-SENSE: NO

( i x ) FEATURE:
        ( A ) NAME/KEY: misc. feature
        ( B ) LOCATION:
        ( D ) OTHER INFORMATION: standardname = "5'Primer"

( x i ) SEQUENCE DESCRIPTION: SEQ ID NO:3:

```
         CGGGAATTCA  ATGCCTGTAC  CAAATCCTAC  AATG                          34
```

( 2 ) INFORMATION FOR SEQ ID NO:4:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear -continued (i i) MOLECULE TYPE: cDNA (i i i) HYPOTHETICAL: NO (i v) ANTI-SENSE: YES (i x) FEATURE:
  (A) NAME/KEY: misc. feature
  (B) LOCATION:
  (D) OTHER INFORMATION: standardname = "3'Primer"

(x i) SEQUENCE DESCRIPTION: SEQ ID NO:4:

CCCGAAGCTT CCTGCAGTTA ACAGGCGGTG ACGGTAATTT CTGCAAC    47